(12) United States Patent
Yamaya

(10) Patent No.: US 12,064,094 B2
(45) Date of Patent: Aug. 20, 2024

(54) ENDOSCOPE CLEANING INSTRUMENT

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 777 days.

(21) Appl. No.: 17/123,317

(22) Filed: Dec. 16, 2020

(65) Prior Publication Data

US 2021/0127965 A1 May 6, 2021

Related U.S. Application Data

(63) Continuation of application No. PCT/JP2018/024677, filed on Jun. 28, 2018.

(51) Int. Cl.
*A61B 1/12* (2006.01)
*A61B 1/00* (2006.01)
*A61B 1/005* (2006.01)

(52) U.S. Cl.
CPC .......... *A61B 1/126* (2013.01); *A61B 1/00087* (2013.01); *A61B 1/0055* (2013.01); *A61B 1/122* (2013.01); *A61B 1/125* (2013.01)

(58) Field of Classification Search
CPC .............................................. A61B 1/121–125
See application file for complete search history.

(56) References Cited

U.S. PATENT DOCUMENTS

| 5,313,934 A * | 5/1994 | Wiita | A61B 1/127 600/109 |
| 5,386,817 A * | 2/1995 | Jones | A61B 1/00135 600/125 |
| 5,662,588 A * | 9/1997 | Iida | A61B 1/00091 600/125 |
| 2002/0010385 A1* | 1/2002 | Ishibiki | A61B 1/00105 600/130 |
| 2011/0230716 A1* | 9/2011 | Fujimoto | G02B 27/0006 600/121 |

(Continued)

FOREIGN PATENT DOCUMENTS

| EP | 3207857 A1 | 8/2017 |
| EP | 3207858 A1 | 8/2017 |

(Continued)

OTHER PUBLICATIONS

International Search Report dated Sep. 4, 2018 issued in PCT/JP2018/024677.

*Primary Examiner* — Matthew J Kasztejna
(74) *Attorney, Agent, or Firm* — Scully, Scott, Murphy & Presser, P.C.

(57) ABSTRACT

An endoscope cleaning instrument detachably attachable to an insertion section of an endoscope from a distal end portion side of the insertion section includes a covering member having a tubular shape and being capable of covering, on an outer circumferential surface of a bending section connected consecutively to a proximal end of a distal end portion in the insertion section, a distal end side adhesive section disposed on a distal end side of the bending section and formed from an adhesive and a proximal end side adhesive section disposed on a proximal end side of the bending section and formed from the adhesive.

12 Claims, 8 Drawing Sheets

(56) References Cited

U.S. PATENT DOCUMENTS

2017/0181611 A1    6/2017  Yamaya
2017/0181612 A1    6/2017  Yamaya

FOREIGN PATENT DOCUMENTS

| | | |
|---|---|---|
| JP | 2015-181914 A | 10/2015 |
| JP | 6239201 B1 | 11/2017 |
| WO | WO 2016/059920 A1 | 4/2016 |
| WO | WO 2016/059921 A1 | 4/2016 |
| WO | WO 2018/037727 A1 | 3/2018 |
| WO | WO 2018/042736 A1 | 3/2018 |

* cited by examiner

ENDOSCOPE CLEANING INSTRUMENT

CROSS REFERENCE TO RELATED APPLICATION

This application is a continuation application of PCT/JP2018/024677 filed on Jun. 28, 2018, the entire contents of which are incorporated herein by this reference.

BACKGROUND OF THE INVENTION

1. Field of the Invention

The present invention relates to an endoscope cleaning instrument detachably attachable to a distal end portion side of an insertion section of an endoscope.

2. Description of the Related Art

In recent years, disease parts present in a digestive tract system and pancreaticobiliary duct system have been observed and treated using a so-called side-viewing endoscope (hereinafter simply referred to as endoscope).

In the endoscope, an observation window and an illumination window are provided in a part of an outer circumference side surface of a distal end rigid member at a distal end portion of an insertion section inserted into a subject.

A configuration in which, on the outer circumference side surface of the distal end rigid member, a cover is put on a position excluding the observation window and the illumination window is also well known.

In the case of endoscopic treatment of a pancreatic duct, a bile duct, a hepatic duct, or the like, a method is usually used in which the distal end portion of the insertion section of the endoscope is inserted to near a duodenal papilla; subsequently, under X-ray fluoroscopy from near the duodenal papilla, a guide wire is projected to a channel opening section in a channel for treatment instrument insertion, which is a conduit provided in the insertion section, and inserted into the pancreatic duct, the bile duct, or the hepatic duct; and thereafter, a treatment instrument such as a catheter is selectively inserted into the pancreatic duct, the bile duct, or the hepatic duct using the guide wire as a guide.

A configuration in which a guide wire or a treatment instrument is inserted into the pancreatic duct, the bile duct, or the hepatic duct via the channel opening section using a raising base (forceps elevator) provided in the distal end portion is also well known.

By being raised, the raising base changes a traveling direction of the guide wire or the treatment instrument inserted through the channel for treatment instrument insertion.

The raising base is turnably axially supported with respect to the distal end rigid member. Rising and falling of the raising base is generally performed by turning of the raising base by an operation wire, which is inserted through the insertion section and a distal end of which is fixed to the raising base, being pulled and loosened by a raising base operation knob provided in the operation section of the endoscope.

The side-viewing endoscope needs to be cleaned and disinfected in order to be used again after use. However, in the distal end rigid member, as explained above, many members having unevenness such as the observation window, the illumination window, the raising base, and the channel opening section are provided.

Accordingly, in order to surely clean and disinfect even these kinds of unevenness, cleaning and disinfection treatment for members forming distal end portions of the distal end rigid member, the observation window, the illumination window, the raising base, the channel opening section, and the like needs to be separately performed in addition to normal cleaning and disinfection treatment for the endoscope.

Therefore, Japanese Patent Application Laid-Open Publication No. 2015-181914 discloses an endoscope cleaning instrument that can locally supply fluid such as cleaning and disinfection liquid from a fluid supply member to a member that covers a distal end rigid member of a distal end portion and forms distal end portions of the distal end rigid member, an observation window, an illumination window, a raising base, a channel opening section, and the like.

A configuration in which, in the insertion section, a bending section bendable in a plurality of directions is connected consecutively to a proximal end of the distal end portion is well known.

An outer coat made of rubber or the like forming an outer circumferential surface of the bending section is wound with threads in a distal end position and a proximal end position of the bending section and thereafter solidified by an adhesive. In other words, a distal end side adhesive section and a proximal end adhesive section where thread-wound parts are solidified by the adhesive are disposed at a distal end and a proximal end of the bending section.

SUMMARY OF THE INVENTION

An endoscope cleaning instrument according to an aspect of the present invention is an endoscope cleaning instrument detachably attachable to a distal end portion side of an insertion section of an endoscope, the endoscope cleaning instrument including a covering member having a tubular shape and being capable of covering, on an outer circumferential surface of a bending section connected consecutively to a proximal end of a distal end portion in the insertion section, a distal end side adhesive section disposed on a distal end side of the bending section and formed from an adhesive and a proximal end side adhesive section disposed on a proximal end side of the bending section and formed from the adhesive.

DETAILED DESCRIPTION OF THE PREFERRED EMBODIMENTS

An embodiment of the present invention is explained below with reference to the drawings. Note that the drawings are schematic. It should be noted that relations between thicknesses and widths of respective members, ratios of thicknesses of the respective members, and the like are different from real ones. It goes without saying that portions having different relations and ratios of dimensions of the drawings are included among the drawings.

Figure 1:
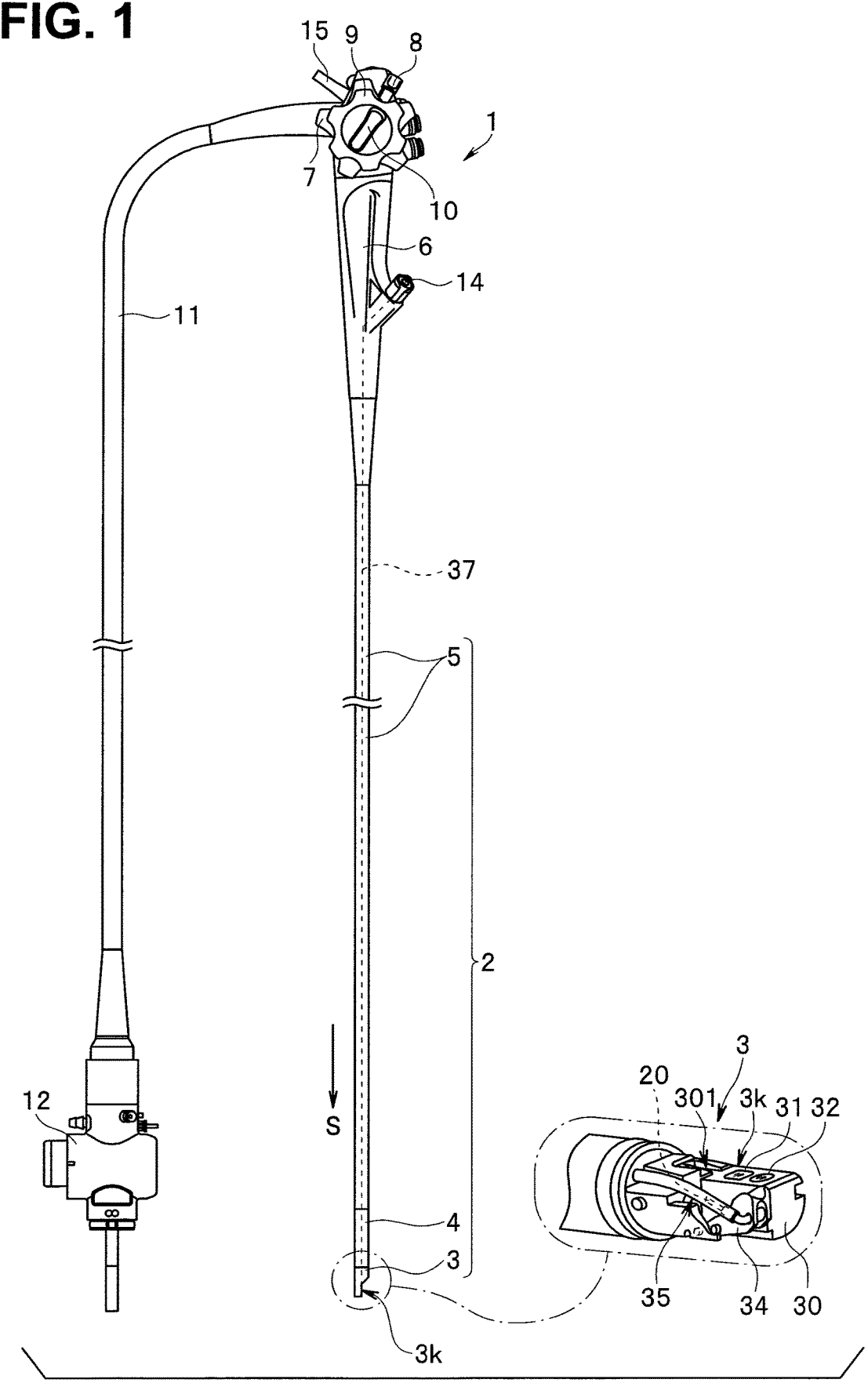
FIG. 1 is a diagram showing an endoscope from which a distal end cover is removed, a distal end portion side of an insertion section of the endoscope being cleaned and disinfected by an endoscope cleaning instrument of an embodiment.

FIG. 1 is a diagram showing an endoscope from which a distal end cover is removed, a distal end portion side of an insertion section of the endoscope being cleaned and disinfected by an endoscope cleaning instrument of this embodiment.

As shown in FIG. 1, a main part of an endoscope 1 includes an insertion section 2 to be inserted into a subject, an operation section 6 connected consecutively to a proximal end side in an insertion direction S of the insertion section 2, a universal cord 11 extended from the operation section 6, and a connector 12 provided on an extension end of the universal cord 11.

Note that the endoscope 1 is electrically connected to a control device and an external device such as an illumination device via the connector 12.

The insertion section 2 includes a distal end portion 3, a bending section 4, and a flexible tube section 5 in order from a distal end side and is formed elongated along the insertion direction S.

An up-and-down bending operation knob 7 for bending the bending section 4 in an up-down direction and a left and right bending operation knob 9 for bending the bending section 4 in a left-right direction are provided in the operation section 6.

A fixing lever 8 for fixing a turning position of the up-and-down bending operation knob 7 and a fixing knob 10 for fixing a turning position of the left and right bending operation knob 9 are provided in the operation section 6.

The bending section 4 is connected consecutively to a proximal end in the insertion direction S of the distal end portion 3. The bending section 4 is bent in, for example, up, down, left, and right four directions by turning operation of the up-and-down bending operation knob 7 and the left and right bending operation knob 9. Consequently, an observation direction of a not-shown image pickup unit provided in the distal end portion 3 is changed. Besides, an insertion property of the distal end portion 3 in the subject is improved.

Further, a raising base operation knob 15 for turning a raising base (forceps elevator) 34 explained below provided in the distal end portion 3 when raising or lowering the raising base 34 is provided in the operation section 6.

A treatment instrument insertion opening 14 for inserting a not-shown guide wire or a not-shown treatment instrument through a channel for treatment instrument insertion 37, which is a conduit, provided along the insertion direction S in the insertion section 2 of the endoscope 1 is provided in the operation section 6.

A distal end rigid member 30 forming the distal end portion 3 and made of, for example, metal is provided in the distal end portion 3.

A recessed cutout section 3k obtained by cutting out one outer circumferential surface side of the distal end rigid member 30 is formed on an outer circumferential surface of the distal end portion 3.

An air/water feeding channel opening section 301, which is an opening of the distal end portion 3 of an air/water feeding channel 300, is formed on one outer circumferential surface of the cutout section 3k.

An observation window 31 and an illumination window 32 are provided on one outer circumferential surface of the cutout section 3k and near the air/water feeding channel opening section 301.

Note that a distal end cover 90 (see FIG. 6) explained below that covers the distal end rigid member 30 excluding the raising base 34, a channel opening section 35, the observation window 31, and the illumination window 32 is provided around the distal end rigid member 30.

Further, the raising base 34 is provided in a position facing the channel opening section 35 in the distal end rigid member 30.

The raising base 34 changes a traveling direction of the treatment instrument or the guide wire, which is inserted through the channel for treatment instrument insertion 37 from the treatment instrument insertion opening 14, from the insertion direction S to the air/water feeding channel opening section 301 side. Consequently, the raising base 34 guides the treatment instrument or the guide wire to a desired position in the subject according to raising of the raising base 34.

The raising base 34 is capable of rising or falling by, in response to turning operation of the raising base operation knob 15, being pulled or loosened along the insertion direction S of a wire 20 inserted through the insertion section 2 and the operation section 6.

Subsequently, a configuration of the endoscope cleaning instrument in this embodiment is explained with reference to FIG. 2 to FIG. 11.

Figure 2:
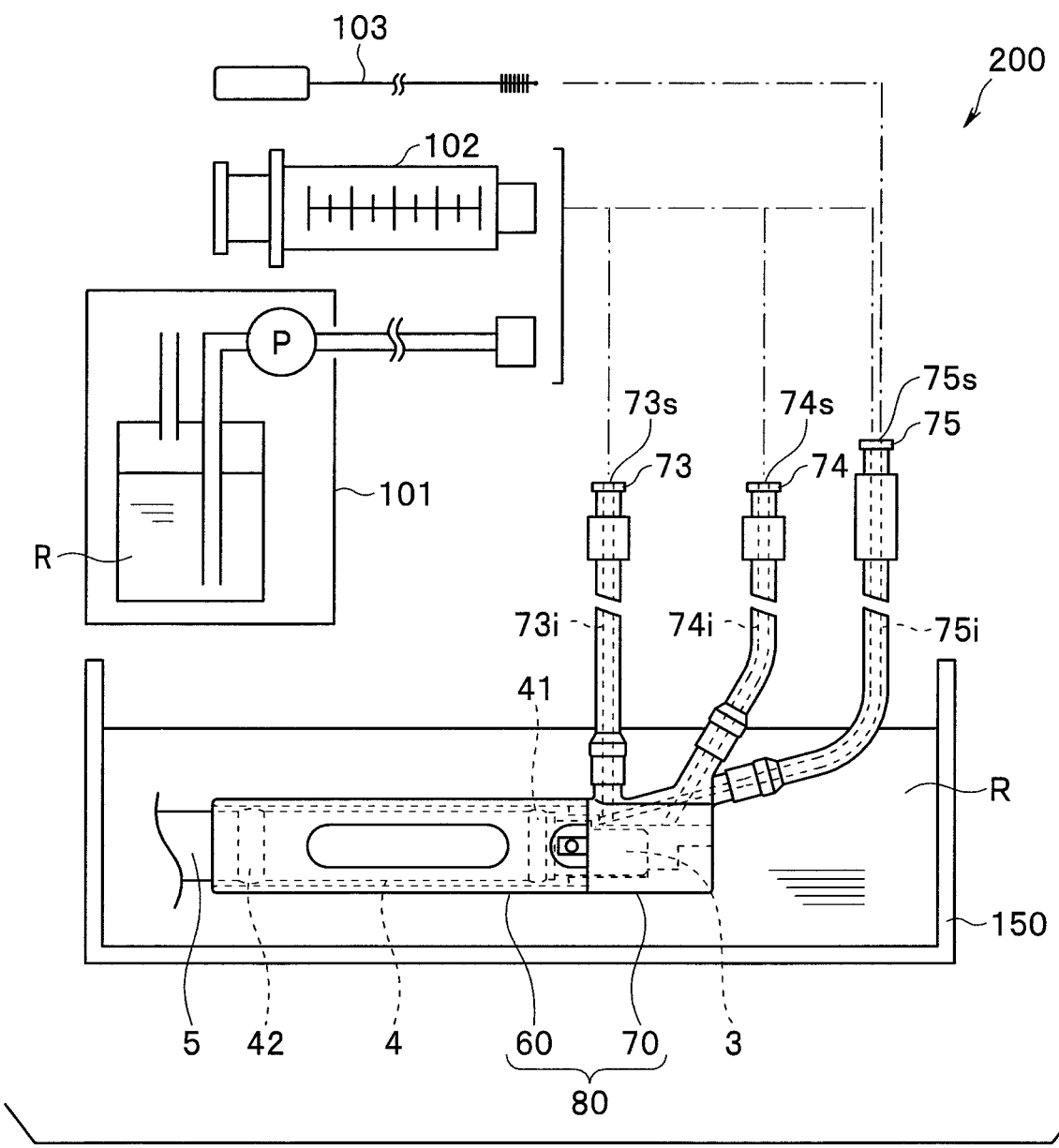
FIG. 2 is diagram showing a cleaning and disinfecting system that cleans and disinfects, using the endoscope cleaning instrument, a distal end portion side of the endoscope shown in FIG. 1 from which the distal end cover is removed.
Figure 3:
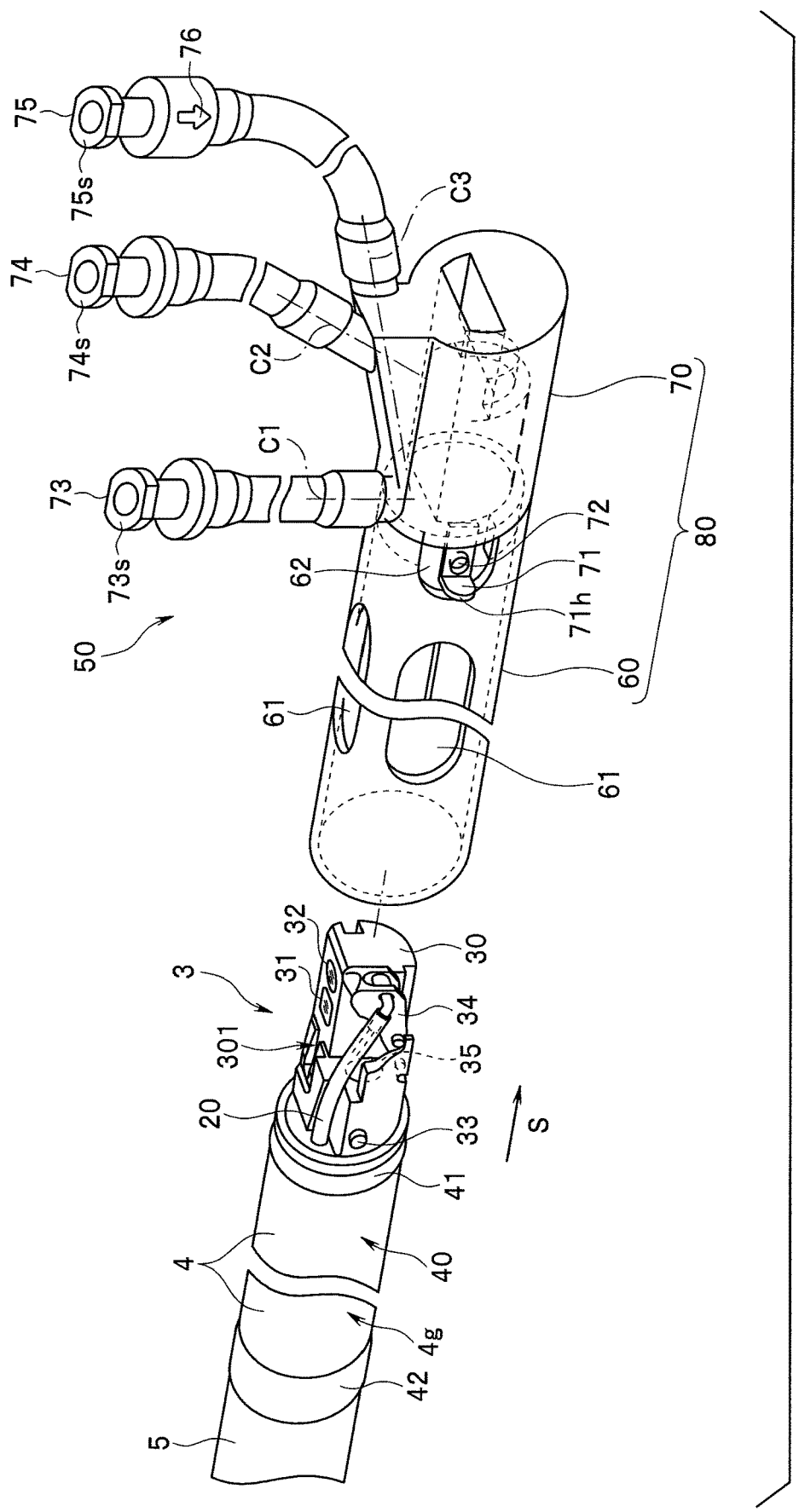
FIG. 3 is a partial perspective view showing a distal end side of the insertion section of the endoscope shown in FIG. 1 and the endoscope cleaning instrument.

FIG. 2 is diagram showing a cleaning and disinfecting system that cleans and disinfects, using the endoscope cleaning instrument, a distal end portion side of the endoscope from which the distal end cover is removed shown in FIG. 1. FIG. 3 is a partial perspective view showing a distal end side of the insertion section of the endoscope shown in FIG. 1 and the endoscope cleaning instrument.

Figure 4:
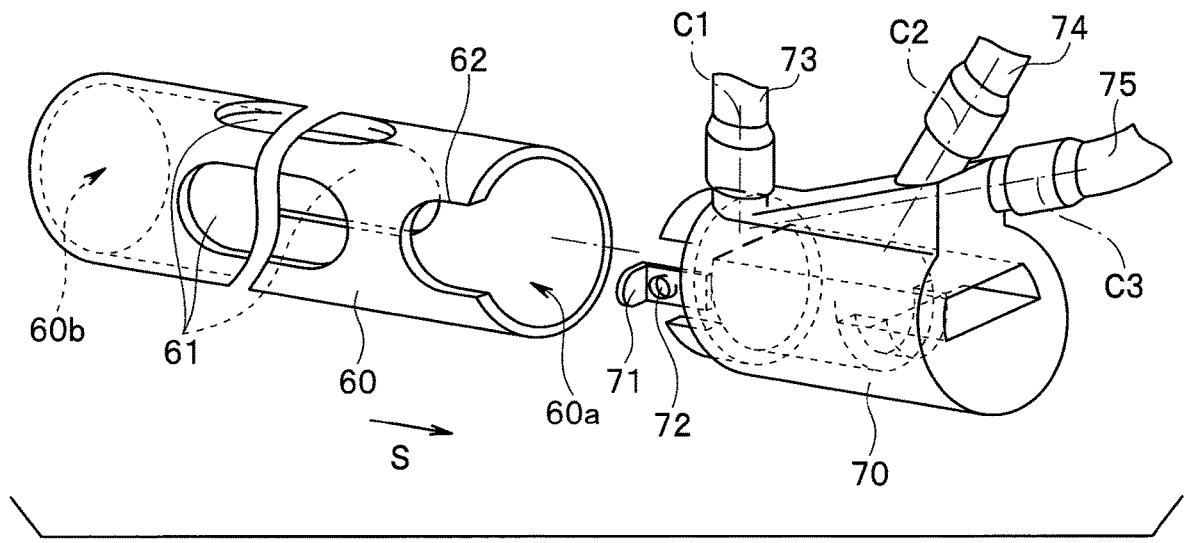
FIG. 4 is an exploded perspective view of the endoscope cleaning instrument shown in FIG. 3.
Figure 5:
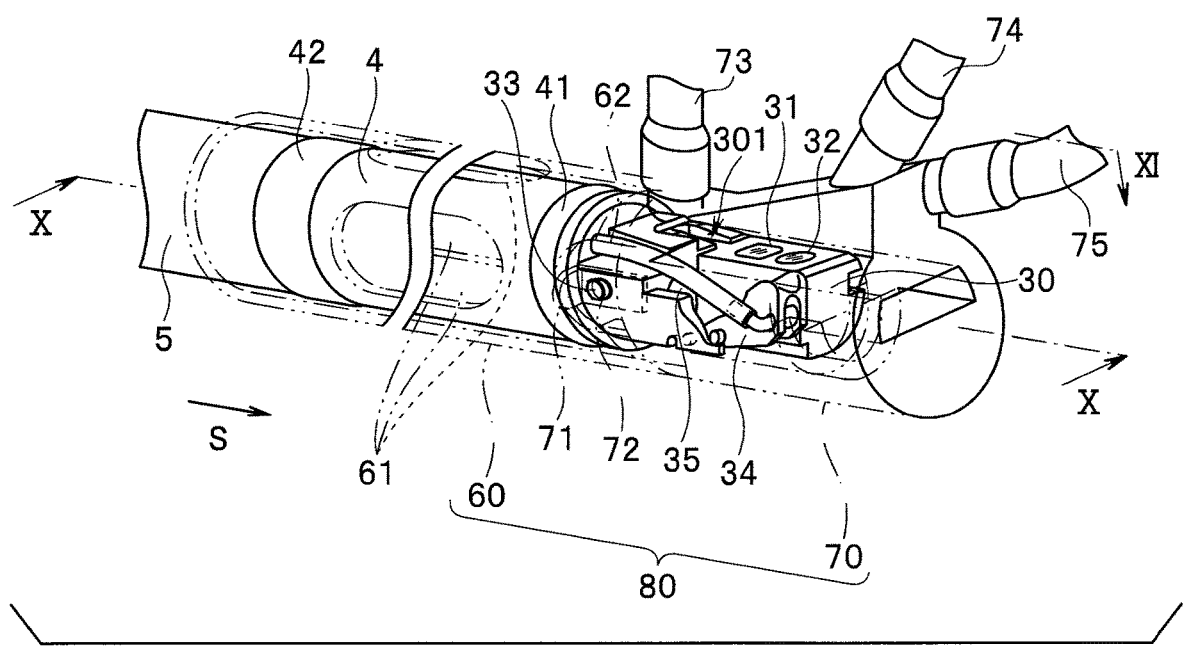
FIG. 5 is a partial perspective view showing a state in which the endoscope cleaning instrument shown in FIG. 3 is attached to the distal end side of the insertion section of the endoscope.

FIG. 4 is an exploded perspective view of the endoscope cleaning instrument shown in FIG. 3. FIG. 5 is a partial perspective view showing a state in which the endoscope cleaning instrument shown in FIG. 3 is attached to the distal end side of the insertion section of the endoscope.

Figure 6:
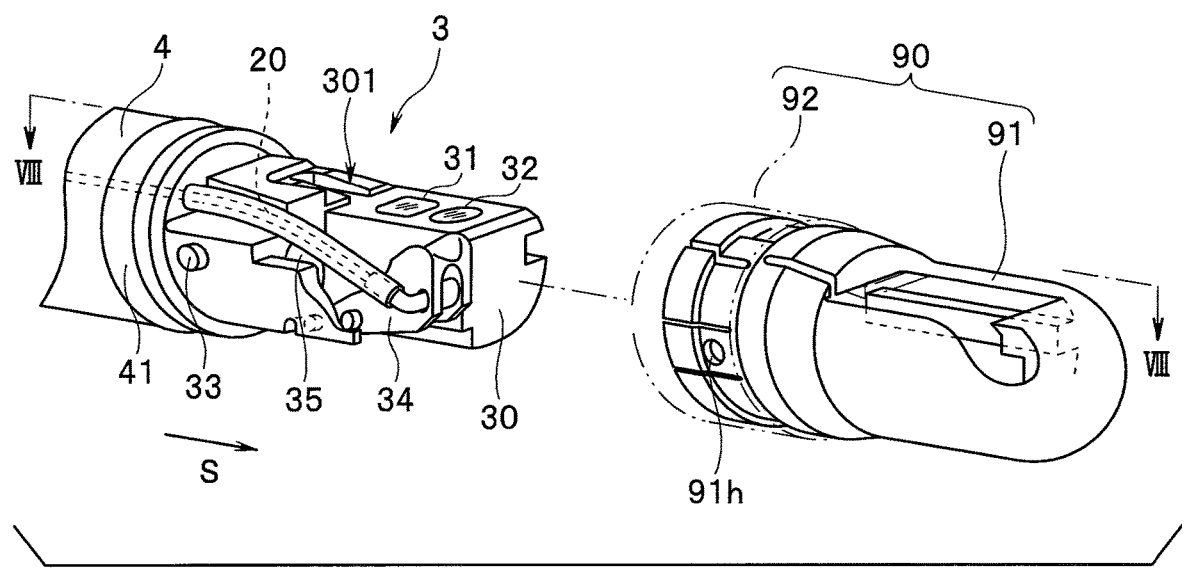
FIG. 6 is a partially exploded perspective view showing a state before the distal end cover is attached to the distal end portion of the insertion section of the endoscope shown in FIG. 1.
Figure 7:
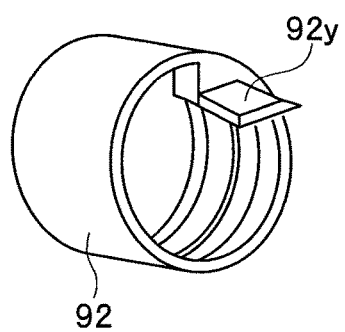
FIG. 7 is a perspective view showing a second cover removed from a first cover in the distal end cover shown in FIG. 6.

FIG. 6 is a partially exploded perspective view showing a state before the distal end cover is attached to the distal end portion of the insertion section of the endoscope shown in FIG. 1. FIG. 7 is a perspective view showing a second cover removed from a first cover in the distal end cover shown in FIG. 6.

Figure 8:
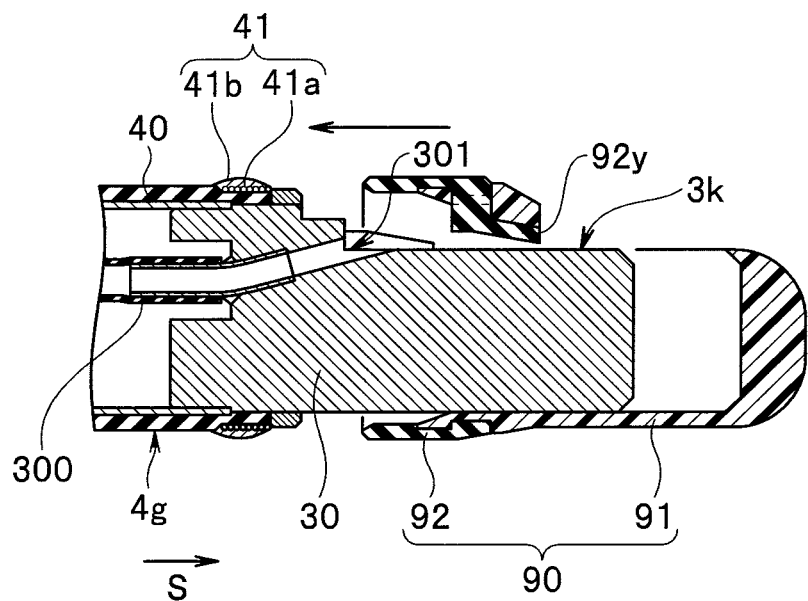
FIG. 8 is a partial sectional view showing a state halfway in attaching the distal end cover to the distal end portion of the insertion section of the endoscope taken along a VIII-VIII line in FIG. 6.
Figure 9:
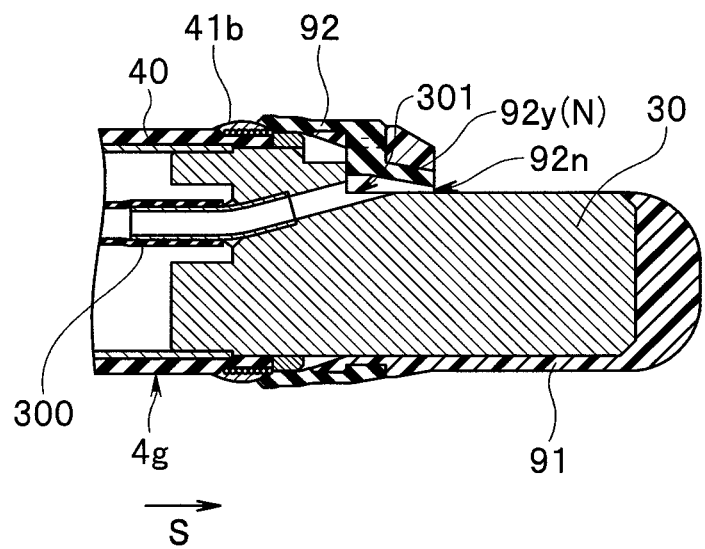
FIG. 9 is a partial sectional view showing a state in which the distal end cover is attached to the distal end portion of the insertion section of the endoscope shown in FIG. 8.

FIG. 8 is a partial sectional view showing a state halfway in attaching the distal end cover to the distal end portion of the insertion section of the endoscope taken along a VIII-VIII line in FIG. 6. FIG. 9 is a partial sectional view showing a state in which the distal end cover is attached to the distal end portion of the insertion section of the endoscope shown in FIG. 8.

Figure 10:
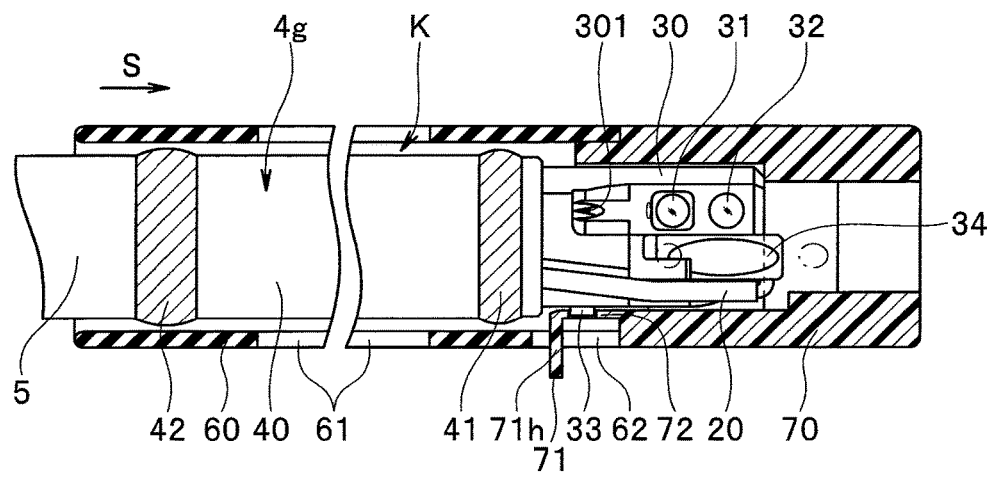
FIG. 10 is a partial sectional view of the distal end side of the insertion section of the endoscope and the endoscope cleaning instrument taken along a X-X line in FIG. 5.
Figure 11:
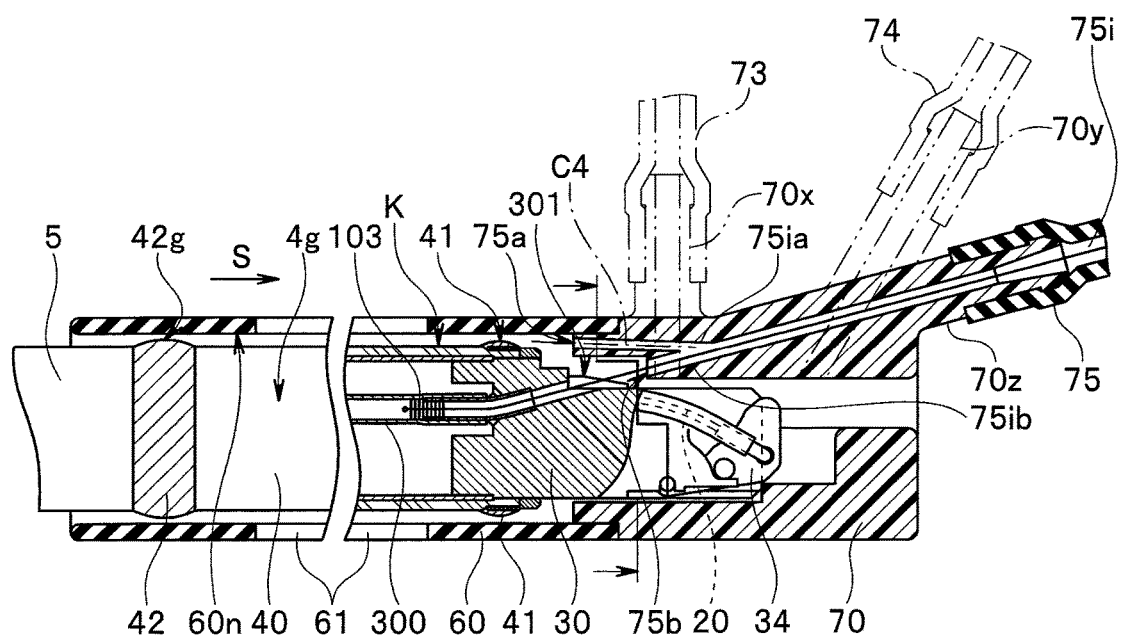
FIG. 11 is a partial sectional view of the distal end side of the insertion section of the endoscope and the endoscope cleaning instrument taken along a X-XI line in FIG. 5.

FIG. 10 is a partial sectional view of the distal end side of the insertion section of the endoscope and the endoscope cleaning instrument taken along an X-X line in FIG. 5. FIG. 11 is a partial sectional view of the distal end side of the insertion section of the endoscope and the endoscope cleaning instrument taken along an X-XI line in FIG. 5.

As shown in FIG. 3 to FIG. 5, an endoscope cleaning instrument 50 is detachable from the distal end portion 3 side in a state in which the distal end cover 90 explained below is removed from the distal end rigid member 30 (see a left figure of FIG. 6) with respect to the distal end side of the insertion section 2 of the endoscope 1. The endoscope cleaning instrument 50 includes a cleaning instrument main body 80.

Note that, in the following explanation, it is assumed that, in all cases in which the cleaning instrument main body 80 is attached to the distal end side of the insertion section 2, the distal end cover 90 is detached from the distal end rigid member 30.

When the endoscope 1 is cleaned and disinfected, in a state in which the cleaning instrument main body 80 is attached to the distal end side of the insertion section 2 as shown in FIG. 5, the cleaning instrument main body 80 is immersed, together with the endoscope 1, in fluid R stored in a cleaning and disinfection tank 150 of a cleaning and disinfecting system 200 as shown in FIG. 2. Note that examples of the fluid R include chemical solution such as cleaning liquid or disinfection liquid.

A main part of the cleaning instrument main body 80 includes a rear side member 60, which is a covering member, and a front side member 70, which is a fluid supply member that supplies the fluid R to the distal end portion 3. Note that the rear side member 60 and the front side member 70 may be integrally formed.

The rear side member 60 is formed in a tube shape from a soft member such as polysulfone or silicon to include openings 60a and 60b at a distal end and a proximal end in the insertion direction S.

A plurality of holes 61 are formed on an outer circumferential surface of the rear side member 60. The holes 61 are holes for making it easy to discharge filth between the cleaning instrument main body 80 and the distal end side of the insertion section 2 when, as shown in FIG. 2, the cleaning instrument main body 80 is immersed in the chemical solution in the cleaning and disinfection tank 150 attached to the distal end side of the insertion section 2.

Further, as shown in FIG. 3 to FIG. 5, an opening window 62 for exposing an operation piece 71 explained below provided in the front side member 70 to an outside of the cleaning instrument main body 80 is formed in a position communicating with the opening 60a on the outer circumferential surface of the rear side member 60.

The rear side member 60 is formed along the insertion direction S in length for covering at least the bending section 4 when the cleaning instrument main body 80 is attached to the distal end side of the insertion section 2 as shown in FIG. 5.

More specifically, as shown in FIG. 8, an outer coat 40 made of rubber or the like forming an outer circumferential surface 4g of the bending section 4 is wound with a thread 41a on an outer circumference of the distal end rigid member 30 in a distal end position on the outer circumferential surface 4g of the bending section 4 and thereafter fixed by an adhesive 41b.

In other words, a distal end side adhesive section 41 obtained by solidifying the wound thread 41a with the adhesive 41b is disposed at a distal end on the outer circumferential surface 4g of the bending section 4.

As shown in FIG. 3, like the distal end side adhesive section 41, the outer coat 40 is wound with a not-shown thread on a distal end outer circumference of the flexible tube section 5 and thereafter fixed by a not-shown adhesive in a proximal end position on the outer circumferential surface 4g of the bending section 4.

In other words, a proximal end side adhesive section 42 obtained by solidifying the wound thread with an adhesive is disposed at a proximal end on the outer circumferential surface 4g of the bending section 4.

The rear side member 60 is formed in length capable of covering both of the distal end side adhesive section 41 and the proximal end side adhesive section 42 in the insertion direction S as shown in FIG. 5, FIG. 10, and FIG. 11 when the cleaning instrument main body 80 is attached to the distal end side of the insertion section 2 as shown in FIG. 5.

Further, the rear side member 60 covers an outer circumference of the bending section 4 to form a gap K between an outer circumferential surface 41g of the distal end side adhesive section 41 and an outer circumferential surface 42g of the proximal end side adhesive section 42 and an inner circumferential surface 60n of the rear side member 60 when the cleaning instrument main body 80 is attached to the distal end side of the insertion section 2 as shown in FIG. 10 and FIG. 11.

Consequently, as shown in FIG. 2, the chemical solution is supplied to the gap K as well in the state in which the cleaning instrument main body 80 is immersed in the chemical solution in the cleaning and disinfection tank 150 as shown in FIG. 2. Accordingly, the chemical solution can be sufficiently brought into contact with the surfaces of the distal end side adhesive section 41 and the proximal end side adhesive section 42. Therefore, a sure cleaning and disinfection effect can be expected for both the adhesive sections 41 and 42.

As shown in FIG. 3 and FIG. 4, the front side member 70 is fixable or detachably attachable to the opening 60a of the rear side member 60 and made of, for example, plastic.

Fluid supply ports 73, 74, and 75 are provided in the front side member 70. Note that, as shown in FIG. 11, the respective ports 73 to 75 are fixable or detachably attachable to respective connection ports 70x, 70y, and 70z of the front side member 70.

The fluid supply ports 73 to 75 and the connection ports 70x to 70z respectively include conduits 73i, 74i, and 75i inside as shown in FIG. 2.

In the fluid supply ports 73 to 75, a cleaning machine 101, a syringe 102, or the like incorporating a pump is connectable to respective port connection openings 73s, 74s, and 75s, which are openings of the respective conduits 73i to 75i.

Further, in the fluid supply ports 73 to 75, the fluid R can flow into the conduits 73i to 75i from the cleaning machine 101 or the syringe 102 connected to the conduits 73i to 75i.

Note that the supply of the fluid R via the fluid supply ports 73 to 75 is not always performed in the cleaning and disinfection treatment for the endoscope 1 but is temporarily performed when the distal end portion 3 is cleaned and disinfected. Accordingly, the supply of the fluid R via the fluid supply ports 73 to 75 is not performed in a state in which the distal end portion 3 is immersed in the chemical solution in the cleaning and disinfection tank 150 but is performed before the distal end portion 3 is immersed.

A brush 103 for cleaning the air/water feeding channel 300 is insertable into and removable from the conduit 75i of the fluid supply port 75 via the port connection opening 75s.

In the fluid supply port 73, a center axis C1 of a fluid supply opening, which is an opening of the conduit 73i, is opposed to a guide plane of the raising base 34 for guiding the treatment instrument or the guide wire when the cleaning instrument main body 80 is attached to the distal end side of the insertion section 2 as shown in FIG. 5. Consequently, the fluid R is supplied to the guide plane from the fluid supply opening.

In the fluid supply port 74, a center axis C2 of a fluid supply opening, which is an opening of the conduit 74i, is opposed to a rear surface side of the raising base 34 when the cleaning instrument main body 80 is attached to the distal end side of the insertion section 2 as shown in FIG. 5. Consequently, the fluid R is supplied from the fluid supply opening to the rear surface side.

The fluid supply port 75 is a port for supplying the fluid R and the brush 103 to the air/water feeding channel 300 via the air/water feeding channel opening section 301 and supplying the fluid R to the gap K when the cleaning instrument main body 80 is attached to the distal end side of the insertion section 2 as shown in FIG. 5.

More specifically, in the fluid supply port 75, the conduit 75i is divided into two conduits 75ia and 75ib in the connection port 70z as shown in FIG. 11.

A first supply opening 75a of one conduit 75ia is formed such that an extension line of a center axis C4 is opposed to the gap K when the cleaning instrument main body 80 is attached to the distal end side of the insertion section 2 as shown in FIG. 5. A second supply opening 75b of the other conduit 75ib is formed such that an extension line of a center axis C3 is opposed to the air/water feeding channel opening section 301.

Accordingly, the fluid R fed into the conduit 75i via the port connection opening 75s is supplied to the gap K from the first supply opening 75a of the conduit 75ia.

Consequently, in the state in which the cleaning instrument main body 80 is immersed in the chemical solution in the cleaning and disinfection tank 150 as shown in FIG. 2, even if air bubbles and the like are mixed in the gap K, the air bubbles and the like can be surely removed from the gap K by the supply of the fluid R. Further, a sure cleaning and disinfection effect for the outer circumferential surface 4g of the bending section 4 can be expected.

The fluid R is supplied to the air/water feeding channel 300 from the second supply opening 75b of the conduit 75ib via the air/water feeding channel opening section 301.

Further, the brush 103 inserted through the conduit 75i via the port connection opening 75s is introduced into the air/water feeding channel 300 from the second supply opening 75b of the conduit 75ib via the air/water feeding channel opening section 301.

At this time, the extension line of the center axis C3 is opposed to the air/water feeding channel opening section 301 and the conduit 75ib and the conduit 75i are coaxially formed. Accordingly, an operator can easily introduce the brush 103 into the air/water feeding channel 300 via the conduits 75i and 75ib, the second supply opening 75b, and the air/water feeding channel opening section 301 simply by inserting the brush 103 from the port connection opening 75s.

Note that, as shown in FIG. 2 and FIG. 3, the fluid supply port 75 is formed larger than the fluid supply ports 73 and 74.

Consequently, it is possible to cause the operator to easily visually recognize that a port into which the brush 103 is inserted among the three ports 73 to 75 is the fluid supply port 75.

Note that, as shown in FIG. 3, an indicator 76 may be provided in the port 75 to thereby cause the operator to visually recognize that the port into which the brush 103 is inserted is the fluid supply port 75.

The conduits 75ia and 75ib are shown as being divided from the conduit 75i but may be respectively individually provided in the fluid supply port 75 and the connection port 70z.

As shown in FIG. 3 to FIG. 5, an L-shaped operation piece 71 including an engagement hole 72 is provided in the front side member 70.

In the operation piece 71, as shown in FIG. 10, a grasping section 71h is extended to the outside of the cleaning instrument main body 80 by the opening window 62 explained above and the grasping section 71h is exposed to the outside of the cleaning instrument main body 80 by the opening window 62.

Consequently, in the state in which the cleaning instrument main body 80 is immersed in the chemical solution in the cleaning and disinfection tank 150 as shown in FIG. 2, the chemical solution can be brought into contact with the operation piece 71 as well by the opening window 62.

When the cleaning instrument main body 80 is attached to the distal end side of the insertion section 2 as shown in FIG. 5, the engagement hole 72 is engaged with an engagement pin 33 formed in the distal end rigid member 30, whereby the operation piece 71 locks the cleaning instrument main body 80 to the distal end side of the insertion section 2.

Further, the grasping section 71h is tilted by the operator from the state in which the cleaning instrument main body 80 is attached to the distal end side of the insertion section 2 as shown in FIG. 5, whereby the operation piece 71 is used to release an engaged state of the engagement hole 72 with the engagement pin 33 and remove the cleaning instrument main body 80 from the distal end side of the insertion section 2 as shown in FIG. 3.

Note that, when the endoscope 1 is normally used, that is, when cleaning and disinfection is not performed, the cleaning instrument main body 80 is not attached to the distal end side of the insertion section 2. The distal end cover 90 is attached to the distal end rigid member 30 as shown in FIG. 9. Note that the distal end cover 90 may be disposable.

The distal end cover 90 is attached from the distal end rigid member 30 side as shown in FIG. 6 and FIG. 8 and includes a first cover 91 and a second cover 92 as shown in FIG. 6.

The first cover 91 is made of, for example, plastic. A locking hole 91h formed on an outer circumferential surface of the first cover 91 is engaged with the engagement pin 33 of the distal end rigid member 30, whereby the distal end cover 90 is locked to the distal end rigid member 30.

In other words, the engagement pin 33 functions as both of a pin for locking of the distal end cover 90 and a pin for locking of the cleaning instrument main body 80.

The second cover 92 is made of, for example, rubber and formed in a ring shape and is fit in an outer circumference on a proximal end side of the first cover 91.

The second cover 92 includes a roof section 92y at a distal end in the insertion direction S as shown in FIG. 7.

When the distal end cover 90 is attached to the distal end rigid member 30 as shown in FIG. 9, the roof section 92y is located in a front of the air/water feeding channel opening section 301 and covers the front of the air/water feeding channel opening section 301.

Consequently, a nozzle opening section 92n communicating with the air/water feeding channel opening section 301 is formed between the roof section 92y and the cutout section 3k. In other words, the roof section 92y functions as a nozzle N.

The nozzle opening section 92n is an opening section for, in the normal use of the endoscope 1, locally supplying fluid supplied to the air/water feeding channel 300 to the observation window 31 and the illumination window 32.

Note that, since the nozzle N is formed in the distal end cover 90, when the distal end cover 90 is removed from the distal end rigid member 30, the nozzle N is detached from the distal end rigid member 30. In other words, the nozzle N is taken away from the front of the air/water feeding channel opening section 301. The air/water feeding channel opening section 301 is exposed.

Consequently, when the cleaning instrument main body 80 is attached to the distal end side of the insertion section 2 and the brush 103 is supplied to the air/water feeding channel 300 from the second supply opening 75b via the air/water feeding channel opening section 301, the brush 103 can be easily inserted into the air/water feeding channel 300 since the nozzle N does not interfere.

In this way, in this embodiment, the rear side member 60 of the cleaning instrument main body 80 is shown as being formed in length for covering the distal end side adhesive section 41 and the proximal end side adhesive section 42 when the cleaning instrument main body 80 is attached to the distal end side of the insertion section 2.

Consequently, in the state in which the cleaning instrument main body 80 is attached to the distal end side of the insertion section 2, when the endoscope 1 is placed in the cleaning and disinfection tank 150 as shown in FIG. 2, the distal end side adhesive section 41 and the proximal end side adhesive section 42 are covered by the rear side member 60. Therefore, the distal end side adhesive section 41 and the proximal end side adhesive section 42 do not come into contact with the cleaning and disinfection tank 150.

In other words, since surfaces of the distal end side adhesive section 41 and the proximal end side adhesive section 42 are not scratched, it is possible to reduce deterioration speed of the adhesive forming the distal end side adhesive section 41 and the proximal end side adhesive section 42.

Further, when the endoscope 1 is immersed in the chemical solution for a fixed time in the cleaning and disinfection tank 150, naturally, the distal end side adhesive section 41 and the proximal end side adhesive section 42 come into contact with the chemical solution introduced into the gap K.

However, since the distal end side adhesive section 41 and the proximal end side adhesive section 42 are covered by the rear side member 60, fresh fluid R having a strong chemical attack property is not always supplied. Therefore, it is possible to reduce the deterioration speed of the adhesive forming the distal end side adhesive section 41 and the proximal end side adhesive section 42.

Consequently, it is possible to provide the endoscope cleaning instrument 50 that can improve durability against the cleaning and disinfection treatment of the distal end side adhesive section 41 and the proximal end side adhesive section 42 exposed to the outer circumferential surface 4g of the bending section 4.

Figure 12:
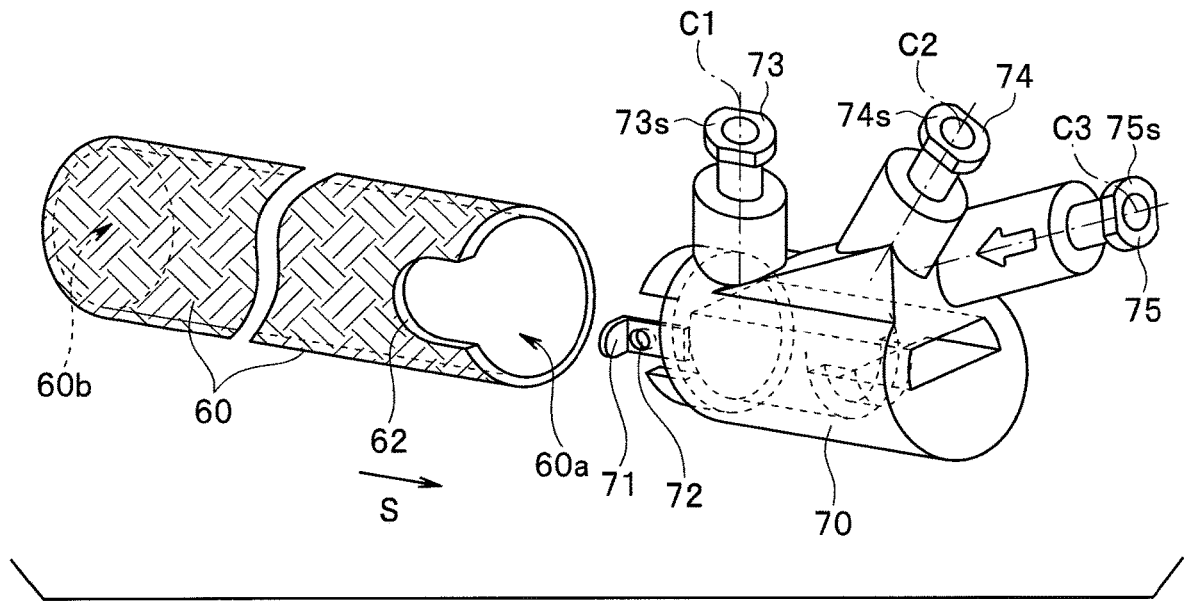
FIG. 12 is a perspective view showing a modification in which a rear side member in a cleaning instrument main body of the endoscope cleaning instrument shown in FIG. 4 is composed of a reticular tube.

Note that a modification is explained below with reference to FIG. 12. FIG. 12 is a perspective view showing a modification in which a rear side member in a cleaning instrument main body of the endoscope cleaning instrument shown in FIG. 4 is composed of a reticular tube.

As shown in FIG. 12, the rear side member 60 may be composed of a reticular tube having flexibility.

Consequently, the rear side member 60 can be manufactured more inexpensively than when the rear side member 60 is made of polysulfone, silicon, or the like. Besides, there is an advantage that the fluid R is easily introduced into an inside from meshes. Further, since the rear side member 60 is flexible, the rear side member 60 easily follows bending of the bending section 4.

Figure 13:
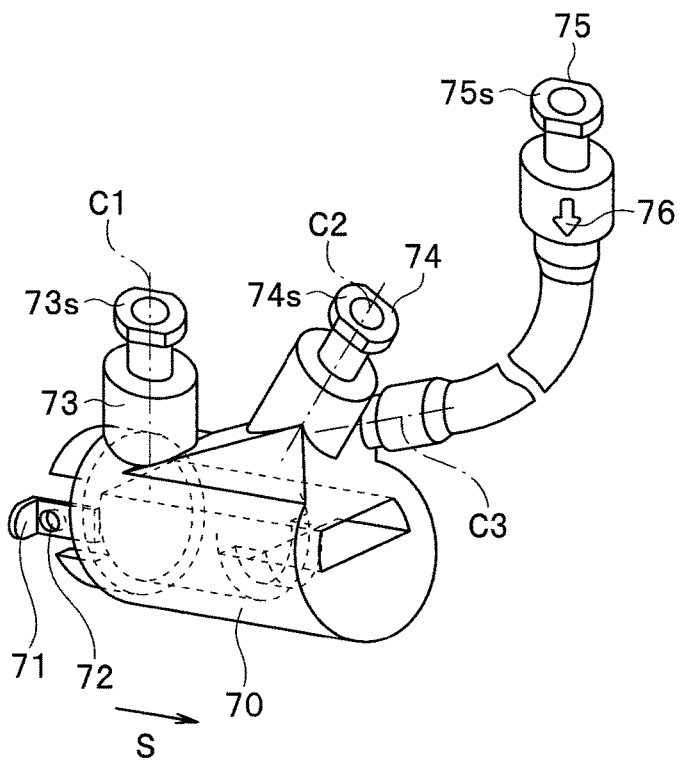
FIG. 13 is a perspective view showing a modification in which only a fluid supply port, through which a brush is inserted, of the endoscope cleaning instrument shown in FIG. 3 is formed longer than other ports.

Another modification is explained below with reference to FIG. 13. FIG. 13 is a perspective view showing a modification in which only a fluid supply port, through which a brush is inserted, of the endoscope cleaning instrument shown in FIG. 3 is formed longer than other ports.

As shown in FIG. 13, in order to cause the operator to easily visually recognize that the port through which the brush is inserted is the fluid supply port 75, the port 75 may be formed longer than the other ports 73 and 74.

In this embodiment explained above, the side-viewing endoscope is explained as an example of the endoscope. However, the endoscope cleaning instrument 50 is also applicable to a front-viewing endoscope in which a raising base is provided in a treatment instrument insertion channel.

Further, it goes without saying that the endoscope cleaning instrument 50 is applicable to not only the endoscope but also a treatment instrument including a raising base at a distal end portion of an insertion section such as a catheter.

The present invention is not limited to the embodiment explained above and can be changed as appropriate within a range not departing from the gist or the idea of the invention read from the claims and the entire specification. An insertion instrument and an endoscope involving such a change are also included in the technical scope of the present invention.

What is claimed is:

1. An endoscope cleaning instrument comprising:
a covering member having a tubular shape, the covering member configured to cover an outer circumferential surface of a distal end portion and a bending section of an insertion section of an endoscope, the bending section being distally located relative to a distal end portion of the insertion section, the covering member having a length configured to cover each of a distal end side adhesive section disposed on a distal end side of the bending section and a proximal end side adhesive section disposed on a proximal end side of the bending section, the covering member including a first hole penetrating from an outer circumferential surface of the covering member to an inner circumferential surface of the covering member; and a fluid supply port located on a distal end side of the covering member;

wherein the first hole is located proximally relative to the fluid supply port, the first hole has a first length and a second length, the first length is a length in a longitudinal direction of the covering member, the second length is a length in a circumferential direction of the covering member, and the first length is longer than the second length.

2. The endoscope cleaning instrument according to claim 1, wherein:

the covering member covers at least the bending section to form a gap between an outer circumferential surfaces of the distal end side adhesive section and the proximal end side adhesive section and an inner circumferential surface of the covering member, and the fluid supply port includes a first fluid supply port including a first supply opening formed toward the gap when the covering member covers the bending section.

3. The endoscope cleaning instrument according to claim 2, wherein the first supply opening is formed such that an extension line of a center axis of the first supply opening is opposed to the gap.

4. The endoscope cleaning instrument according to claim 3, wherein:

the fluid support port includes a second fluid supply port;

the second fluid supply port includes a second supply opening different from the first supply opening, and the second supply opening is formed such that an extension line of a center axis of the second supply opening is opposed to an opening of a conduit in the insertion section formed in the distal end portion of the insertion section.

5. The endoscope cleaning instrument according to claim 1, wherein the covering member is composed of a reticular tube.

6. The endoscope cleaning instrument according to claim 1, wherein the covering member includes a wall on a distal end of the covering member, the wall includes a through hole.

7. The endoscope cleaning instrument according to claim 1, wherein the covering member includes a second hole penetrating from the outer circumferential surface of the covering member to the inner circumferential surface of the covering member, the second hole being located between the fluid supply port and the first hole.

8. The endoscope cleaning instrument according to claim 7, wherein:

the fluid supply port includes a first fluid supply port, a second fluid supply port and a third fluid supply port;

the first fluid supply port is closest to the second hole than the second fluid supply port and the third fluid supply port;

the second fluid supply port is located between the first fluid supply port and the third fluid supply port; and the third fluid supply port is located on a distal end of the covering member.

9. The endoscope cleaning instrument according to claim 8, wherein the first fluid supply port, the second fluid supply port and the third fluid supply port are each located along a longitudinal direction of the covering member.

10. The endoscope cleaning instrument according to claim 8, wherein the first fluid supply port has a first center axis, the second fluid supply port has a second center axis, the third fluid supply port has a third center axis, and the third center axis intersects the first center axis and intersects the second center axis.

11. The endoscope cleaning instrument according to claim 10, wherein the first center axis intersects the third center axis by a first angle, the second center axis intersects the third center axis by a second angle, and the first angle is smaller than the second angle.

12. The endoscope cleaning instrument according to claim 1, wherein the covering member comprises:

a first body comprising the fluid supply port, the first body having a first longitudinal length; and a second body separately formed from the first body, the second body comprising the first hole, the second body having a second longitudinal length longer than the first longitudinal length;

wherein the first body and the second body have mating connection surfaces connecting the first body to the second body.

* * * * *